United States Patent [19]

Briggs et al.

[11] Patent Number: 5,589,611
[45] Date of Patent: Dec. 31, 1996

[54] DISEASE RESISTANCE GENE FROM MAIZE AND ITS USE FOR DISEASE RESISTANCE AS A SELECTABLE MARKER AND AS A GENE IDENTIFICATION PROBE

[75] Inventors: Steven P. Briggs, Des Moines; Gurmukh S. Johal, Urbandale, both of Iowa

[73] Assignee: Pioneer Hi-Bred International, Inc., Des Moines, Iowa

[21] Appl. No.: 123,761

[22] Filed: Sep. 17, 1993

Related U.S. Application Data

[63] Continuation-in-part of Ser. No. 995,658, Dec. 15, 1992, abandoned.
[51] Int. Cl.$^6$ .............................. A01H 1/04; C12N 5/00; C12N 15/00; C07H 21/04
[52] U.S. Cl. .................................. 800/205; 800/DIG. 56; 536/23.6; 435/6; 435/172.3; 435/240.4; 435/243; 435/320.1; 935/9; 935/64; 935/67; 935/79
[58] Field of Search .......................... 435/69.1, 6, 172.1, 435/172.3, 240.4, 243, 320.1; 800/205, DIG. 56; 536/23.1, 23.6, 24.3; 935/9, 67, 72, 92, 64

[56] References Cited

PUBLICATIONS

O E Nelson et al (1964) J Hered 55:194–199 (Abstract).
S J Wolf et al (1990) Crop Sci 30;728–734.
V Walbot (1992) Annu Rev Plant Physiol Plant Mol. Biol 43:49–82.
M Bevan (1984) Nucleic Acids Research 12:8711–8721.
E C Dale et al (1991) Proc Natl Acad Sci USA 88:10558–10562.
M McLaughlin et al (1987) Genetics 117:771–776.
T A Brown (1990) Gene Cloning. 2nd ed. pp.153–177.
S Bagga et al (1992) Plant Molecular Biology 19:951–958.
J Nash et al (1990) Plant Cell 2:1039–1049.
Johal, et al. (1992) Reductase Activity Encoded by the HM1 Disease Resistance Gene in Maize, *Science*, vol. 258, pp. 985–987.
Anzai, et al. (1989) Transgenic Tobacco Resistant to a Bacterial Disease by the Detoxification of a Pathogenic Toxin, *Mol. Gen. Genet.*, 219:492–494.
Raikhel, et al. (1993) The Wide World of Plant Molecular Genetics, *The Plant Cell*, pp. 823–830.
Duvick, et al. (1988) Embryogenic Maize Callus Lines Expressing HC–Toxin Resistance or Susceptibility: A Model System for Study of the HM1 Locus, *Journal of Cellular Biochemistry*, Supp. 12C, p. 279.
Delmotte, et al. (1980) Improved Procedures for Purification of the *Bandeiraea simplicifolia* I Isolectins and *Bandeiraea simplicifolia* II Lectin by Affinity Chromatography, *Eur. J. Biochem.*, vol. 112, pp. 219–223.

*Primary Examiner*—Bruce R. Campell

[57] ABSTRACT

The HM1 gene in maize confers race-specific resistance to the pathogen, *Cochliobolus carbonum*. We have used transposon mutagenesis to tag, clone, and characterize several HM1 alleles. The gene can be used as a selectable marker in conjunction with the toxin produced by *C. carbonum*.

11 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5198 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAATTCGTAT   ATCAGTTTAC   TGCATGTATA   TTTTTTGCAT   GCACATTGGA   AAGACAATTC      60

CTTGATTTAT   GTTGTTCGTA   ATTACCAAAA   AATCAAATCA   TTTATGTTCG   TAATTGCTAG     120

ATTTTTACGT   CTTCCATAAA   ACTGTCCCTA   ATTCTCGCCT   GTTCTTAATT   ACCATAAAAA     180

ATCAAATCAA   ATCACTTATA   GTCTTAACTG   CCAAATTTTT   ATATCTGCCA   TAAAATTGTC     240

CCTAATTTCC   GTCGGCGTTC   TTAGTTGGAC   CGATATTAGG   TTTTTTCAAT   TATGCTACAC     300
```

```
TGTCTAAATA TTTATGCGAC GTTGTATAAG AATTTGTGCT TTGTGTGACT CATGTCATCC    360
AATTTTTTGT GCGCGTGCAG TGGAAAGGAC ATATAATCTA AAATTTGCGT GCATGCAATG    420
GAAACTCCTA CAATTTGCCT TAATTTTTAG ATGTGCATAA AAATAGAAAT TGCATGCATA    480
CGACTCCCAT ATTTTTCAGA TCTGCCATAA AAATAGGATC GTAAATACAA CCCACCAAAC    540
TATCAACCTC TCATATTGGC TCGATATTTA TGTTTATAAC TGAGAGGTTT TATGCCTAAA    600
ACTTAAGGTA TTTACGCTCG AACCTGTAGA TGCATCCACC AGTGAACCAC ATGCCAGATT    660
TTTTACGTAG TATACCACAT TGCATATATA ACTACACCAT GTTGCATAAT TTGTATAAGT    720
ATATATCATA AACTGGTGCT AACGAGCCTA GTTGCATGTC TGTTGAAGCG ATCATATATT    780
TATACACGAA ATAAAGCATT TAAATAATTT TTTTTGTTT TCATGCATGC CAATCCATTT     840
CCTTTCATCG CACATCCTGC CATCCTAAAT TTGTGTGCAT GCATCAAGAA ACAGATTTTT    900
ACACAGTATA CTGAATTGAA TAAATACCTA CACCTTGTAA CATAATTAAT ATCAGTATAT    960
TATAAACTAG TCCTAACGAA TTTAGTTGTA TGGCTGTTGG AGCGATCCTA TATTTATGGA   1020
GAAATAAAG TATTAAATAT TTTTTTTGT TCCATGCAT GCCAATCCAT TTCCTTTCAT      1080
CGCATATTCT TGTCATCTTA AATTGTGCT CATGCAACAG GAAACAAATT TTACGCAGT    1140
GTACCAAATT GCATAAACAC CTACACCGTG TTGCATAATT AGTATCGTTA TATAACATAA   1200
ACTAGTCTTG ACAAGCCTAT CTAAATGGGT TTAGAGTGA TCTTATATTT ATGGAGGAAA    1260
TAAAGCATTA AATATGAATA TTTGTTTCA TACATGACAA TTCATTTCCT TTTATCGTAC    1320
AAATTTTGCC ATCCTAATTT TGTGCACATG CAGCAGGTAA AAAACTTTTA CGTAGTGTAC   1380
CAAATTGCAT AAATATCTAC ACCGTGTAGC ATATTTAGTA TTAGTATATA TATCATAAAC   1440
TGGTCCTAAC GAGCCTAGCT GCATAGCTGT TGCAGCGATC CTATATTTAT GGAGAAAATG   1500
AATCATTTAA AAATAGAAAA AGTCAGAATC TTTTTTTAA AACTTTACGC GTATGCAGGG    1560
ACACATGTTT GACTTATGCA TCCATTCTTT TTTTGCGAGC ATAAACGTGG GGTGGGGAGC   1620
GCACCCGACA AACTGGCTTG GGGAGTGAGT GGGCGCGCCG GCCTGGACCA GGTCGCAGGG   1680
GTGGTCGGCC TGGGCTTCCT CTAACTATTT GAAGCCCAGG GTTCCTAATA TACCTTTCCC   1740
TATATATATA TGGCTTCTTT GGAAGCTTTA CTTAAAAAAC TTTAGCTTTA GCTTTTGAGC   1800
TTCACCATAA AACAACTCCA GCAAATTGTT AAGGTGGGTT TCAGAAGCGT TTGACTTCCA   1860
CATGAACTCC AGCTTCTATA GTACAATTGA TTTGTGTGAG TTTCCTTGAT TACCCTTTAT   1920
GATTAGTGGG TTGTCGCGAG AGAAAACGTA AGTTATATAT TGCGTAACCA GTGGCATGGT   1980
GGGTAATTTT TGTACAACTT CATGAGGAGA TATAAAAACG GTGTTTTGT AGCACCCTCT   2040
AAGAGTTTCA TGAATTTCAT GAAATTGACC TCTAGTTTCG ATTTTTTAA AGCTAGAGCT    2100
CGTGGAGCTG GACCAGTTTA GGTGGAAGAA GTTGGAATGA AGTTGAAATT TTTGAAGTGA   2160
AGCTCTCTCA AATAGAGCGT TAATCTACAT TATTAATATT TGACTTCTAG ATAAGCGAGA   2220
ATGGCACTCT TTAGAATGGA GCAACTGGGC TTAGCTACAT TTATGATATG GAGGTTCTTA   2280
GTTGTATTAT GTAGTTTCTT AGCTACCTTT TATATTTGGA AAACCGAACC AGACTCTGGA   2340
TTGTACATAG CCTTTGAAGA ATTATTCAAG AGTTAATTAA GCTGTAATGC CACTAATATT   2400
AAGGTTTAAT TTACCCTTGT ATTCAATACT TAACGTTATA TATTCTCTAT AATTAAACAT   2460
AGTCCAACTT AAAAAATGAT TTTTGCAAAG ATAGAATTAT ATGTTTTTG TGAGGGCTAA    2520
TAGTTTAATG AAGTTATCGA TGTTTGTATA TTTCACGACT ATAACCTTCA CCTCTGACCG   2580
CTAATGCTTG TTTAGACCAT ATTTGGATGT TGTTGTATTA AAATATTATG TTATTAAGGA   2640
ACCATTGTTT TAGCATTGTA TTCAAAATTA TGAAGTTTTT ATATGCAAAT GATTCACTCG   2700
```

```
AAAAAACAAA  AGTATCAAAA  TCATAGTATT  TTCTCTCTCT  AAAATTCCAA  AAATATTTTA   2760
CATCTAAAGT  TGATGTCTTG  GCCTCCCGCG  CTGTTTTACC  TTCCTCCTCT  GGACACCAAC   2820
CACAGGCCGA  CAACCGAGTA  AGCCGGTCAA  TTTTGGTATC  CTGCTCATGA  CTCATATCAG   2880
GCGGTAGCCG  AGCAGCCGCC  CAGCTTTCTC  ATGCCAGAGC  AAACCCATAG  GTCCAGTCCA   2940
AATCCAATCC  CTGTTGCCAT  CAGAATTTCA  GGGGCAGCCA  TGGCCGAAAA  GGAGAGCAAC   3000
GGAGTGCGGG  TGTGCGTCAC  CGGAGGAGCC  GGGTTCATCG  GCTCCTGGCT  CGTCAGGAAG   3060
CTCCTCGAGA  AAGGCTACAC  CGTCCACGCC  ACCCTGCGGA  ACACCGGTGC  GTCTGATGGC   3120
GGCTCCTCAG  CTCGATCCGC  GCGTCGCGAA  AGGCGAAACA  CGCCAAAGGC  GAAAGGAGTG   3180
GGTCGGGTCT  CGTGTGTGGC  TGCCTGATGA  TTCGGGAATC  TTAGCCGGAT  TCGTGTGCTG   3240
GTGGGTGTGC  AGGGGACGAG  GCGAAGGCGG  GGCTGCTGCG  TCGGCTGGTC  CCCGGCGCGG   3300
CGGAGCGGCT  GCGGTTGTTC  CAGGCCGACC  TCTTCGACGC  CGCCACCTTC  GCGCCGGCGA   3360
TCGCTGGGTG  CCAGTTCGTC  TTCCTCGTCG  CCACGCCATT  CGGGCTCGAT  AGCGCCGGCT   3420
CCCAGGTGAA  GCTTGCCGTC  GCGTTCGCTC  CCTTCACTGT  TTTACTAGTC  AACGAGTGGT   3480
CAGGCGGCGA  CGCGCCGTGC  TGTCTCTTCT  TAATTTTAAG  TTGTGGAAAA  TTACTGTCCT   3540
TGCAAAGGAA  AAATTTGATC  AGACTGAGTA  TGAGTAAAGA  CCAGTAAGAC  AGCACAAGGA   3600
TTGCGAGCTG  CGACTGCGAG  CAGAGGAAAC  GTCTTCACAG  TTATTCTTGT  CTGCCTTGTT   3660
TTTCTCTATC  TGAAGCAAAA  TCTTGTGGTG  CCCATCGACC  GCGTATAGCA  GTATAAGAGC   3720
ACGGCGGAAG  CTGTGGTGGA  CGCGGTGCGC  GCGATCCTCC  GGCAATGCGA  GGAGTCCCGG   3780
ACGGTGAAGC  GAGTGATCCA  CACAGCCTCC  GTAGCGGCCG  CCTCGCCGTT  GCTGGAGGAG   3840
GAGGTCTCCG  CCTCCGGCGT  CGGGTACAGA  GACTTCATCG  ACGAATCTTG  TTGGACTTCG   3900
CTCAACGTTG  ACTATCCTCT  CCGAAGCGCA  CACTTCGACG  TAAGTAGTAT  ACAAGCGAAG   3960
CTTCTTCTGA  TTTCTGAACT  GGAACGCCTG  ATCACATTAA  TATTTTTAG  CTGACGGCCA   4020
TTTGATTTGC  AGAAGTACAT  ACTGTCGAAG  CTGCGGTCAG  AGCAGGAGCT  CCTGAGCTAC   4080
AACGGCGGCG  AGAGCCCGGC  GTTCGAGGTG  GTGACCCTGC  CGCTGGGGCT  CGTGGCGGGC   4140
GACACGGTCC  TCGGCCGCGC  CCCGGAGACG  GTGGAGAGCG  CCGTGGCGCC  CGTGTCCCGC   4200
AGCGAGCCCT  GCTTCGGCCT  CCTGCGCATA  CTGCAGCAGC  TCCTGGGGTC  GCTGCCGCTG   4260
GTGCACGTGG  ACGACGTCTG  CGACGCGCTC  GTCTTCTGCA  TGGAGCGGCG  CCCCTCCGTC   4320
GCCGGCCGCT  TCCTCTGCGC  CGCCGCGTAC  CCGACGATCC  ACGACGTGGT  CGCCCACTAC   4380
GCCAGCAAGT  TCCCTCACCT  CGACATCTTG  AAAGAGTAAG  ATCAAAGCG  TCCACAGCGA   4440
CAGCATCACC  CTGCACACAA  GAACTGACTG  CCGATTTACG  TTTCTGTTGC  GATTGGTTGG   4500
ATTGATCTGC  GTCAGGACGG  AGGCGGTGGC  GACGGTGCGG  CCTGCCCGGG  ACAGGTTGGG   4560
CGAGCTGGGC  TTCAAGTACA  AGTACGGCAT  GGAAGAGATT  CTGGATAGCA  GCGTTGCCTG   4620
TGCGGCGAGA  TTAGGTTCCC  TTGACGCATC  CAAGCTCGGC  CTACAGAAAG  GATAAAAGCT   4680
CGAAGCTTAC  TCATAAGCAC  CATGGGGAAC  TTGGATTGTT  CGCTGTCCAC  TATACGCGTT   4740
CGAAATTTGG  AAACTAGACA  TACTCCAATA  AAACAAGAGG  TAAAGAAACG  TGGGCTAACT   4800
GATACGCGTT  GAGCAGTTGA  GCTAGCCTAG  TTTAGTCCAC  CTGTGTGCAG  GGTTTAAAAC   4860
TTCGACGAAA  TTTTATGACT  TGCGATAATT  TTAGGCCTCT  AAATATCAAC  CATACACTCT   4920
AAATTGTATA  TGTGCATACA  CATATAGCCA  TATGGACGCT  CTGATCTAGC  ATCCTACACC   4980
TATGCACCTC  TCTAAGAACA  ACTCCAACAG  CCTCACTAAA  TATATCAGAT  TCGGTAAAAA   5040
AAAACCCAGT  TAAAATTGTA  TCCAATAGTC  TCGTTTTATT  CTTATCTTCT  CTATCCAACT   5100
```

| | | | | | |
|---|---|---|---|---|---|
| CGTCATATGG | TCCCTTTCGC | TAGACATCTT | TGCCAAGGCG | TACGGCTCGC | CATATCCCTC | 5160 |
| GTCATGCCCA | ACTGTCCTCC | CGCCGTCGCA | GAGAATTC | | | 5198 |

(2) INFORMATION FOR SEQ ID NO:2:

( i ) SEQUENCE CHARACTERISTICS:
        ( A ) LENGTH: 1374 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| GAATTCGGCA | CGAGTGCCAT | CAGAATTTCA | GGGGCAGCCA | TGGCCGAAAA | GGAGAGCAAC | 60 |
| GGAGTGCGGG | TGTGCGTCAC | CGGAGGAGCC | GGGTTCATCG | GCTCCTGGCT | CGTCAGGAAG | 120 |
| CTCCTCGAGA | AAGGCTACAC | CGTCCACGCC | ACCCTGCGGA | ACACCGGGGA | CGAGGCGAAG | 180 |
| GCGGGGCTGC | TGCGTCGGCT | GGTCCCCGGC | GCGGCGGAGC | GGCTGCGGTT | GTTCCAGGCC | 240 |
| GACCTCTTCG | ACGCCGCCAC | CTTCGCGCCG | GCGATCGCTG | GGTGCCAGTT | CGTCTTCCTC | 300 |
| GTCGCCACGC | CATTCGGGCT | CGATAGCGCC | GGCTCCCAGT | ATAAGAGCAC | GGCGGAAGCT | 360 |
| GTGGTGGACG | CGGTGCGCGC | GATCCTCCGG | CAATGCGAGG | AGTCCCGGAC | GGTGAAGCGA | 420 |
| GTGATCCACA | CAGCCTCCGT | AGCGGCCGCC | TCGCCGTTGC | TGGAGGAGGA | GGTCTCCGCC | 480 |
| TCCGGCGTCG | GGTACAGAGA | CTTCATCGAC | GAATCTTGTT | GGACTTCGCT | CAACGTTGAC | 540 |
| TATCCTCTCC | GAAGCGCACA | CTTCGACAAG | TACATACTGT | CGAAGCTGCG | GTCAGAGCAG | 600 |
| GAGCTCCTGA | GCTACAACGG | CGGCGAGAGC | CCGGCGTTCG | AGGTGGTGAC | CCTGCCGCTG | 660 |
| GGGCTCGTGG | CGGGCGACAC | GGTCCTCGGC | CGCGCCCCGG | AGACGGTGGA | GAGCGCCGTG | 720 |
| GCGCCCGTGT | CCCGCAGCGA | GCCCTGCTTC | GGCCTCCTGC | GCATACTGCA | GCAGCTCCTG | 780 |
| GGGTCGCTGC | CGCTGGTGCA | CGTGGACGAC | GTCTGCGACG | CGCTCGTCTT | CTGCATGGAG | 840 |
| CGGCGCCCCT | CCGTCGCCGG | CCGCTTCCTC | TGCGCCGCCG | CGTACCCGAC | GATCCACGAC | 900 |
| GTGGTCGCCC | ACTACGCCAG | CAAGTTCCCT | CACCTCGACA | TCTTGAAAGA | GACGGAGGCG | 960 |
| GTGGCGACGG | TGCGGCCTGC | CCGGGACAGG | TTGGGCGAGC | TGGGCTTCCA | AGTACCAAGT | 1020 |
| ACGGCATGGG | AAGAGATTCT | GGATAGCAGC | GTTGCCTGTG | CGGCGAGATT | AGGTTCCCTT | 1080 |
| GACGCATCCA | AGCTCGGCCT | ACAGAAGGA | TAAAAGCTCG | AAGCTTACTC | ATAAGCACCA | 1140 |
| TGGGGAACTT | GGATTGTTCG | CTGTCCACTA | AACGCGTTCG | AAATTTGGAA | ACTAGACATA | 1200 |
| CTCCAATAAA | ACAAGAGGTA | AAGAAACGTG | GGCTAACTGA | TACGCGTTGA | GCAGTTGAGC | 1260 |
| TAGCCTAGTT | TAGTCCACCT | GTGTGCAGGG | TTTAAAACTT | CGACGAAATT | TTATGACTTG | 1320 |
| CGATAATTTT | AGGCCTCTAA | AAAAAAAAAA | AAAAAAAAAA | AAAAAAACT | CGAG | 1374 |

(2) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:3:

| | | |
|---|---|---|
| CTGCTCATGA | CTCATATCAG | GCGGTAGC | 28 |

-continued ( 2 ) INFORMATION FOR SEQ ID NO:4:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "PRIMER"

( x i ) SEQUENCE DESCRIPTION: SEQ ID NO:4:

GACCAGCCGA CGCAGCAGCC CCGCCTTC 28

DISEASE RESISTANCE GENE FROM MAIZE AND ITS USE FOR DISEASE RESISTANCE AS A SELECTABLE MARKER AND AS A GENE IDENTIFICATION PROBE

CROSS REFERENCE TO RELATED APPLICATION

This is a continuation-in-part of prior application Ser. No. 07/995,658, filed Dec. 15, 1992, now abandoned.

TECHNICAL FIELD

This invention relates to the isolation of a gene which controls resistance to both a fungus and a fungal disease toxin and its use to confer resistance to fungal disease, as a selectable marker and as a probe to identify homologous disease resistance genes in maize and other crops.

BACKGROUND OF THE INVENTION

Disease resistance genes are defined as Mendelian factors that cosegregate with the resistance trait. The gene HM1, which controls resistance to *Cochliobolus carbonum* Nelson race 1 was among the first disease resistance genes to be described. The disease caused by *C. carbonum* race 1 can be devastating, resulting in yield losses of 80% or more due to plant death and grain mold. The dominant allele, Hm1, and the duplicate factor, Hm2 are the only disease resistance genes that are known to be fixed at a high frequency in maize germplasm.

Since the discovery of a race-specific compatibility factor that is produced by the fungus, the disease caused by *C. carbonum* race 1 has been the subject of detailed study. This compatibility factor permits the fungus to infect certain genotypes of maize that would otherwise be resistant. The role of HM1 in providing resistance to the fungus is a function of its ability to cause reduced sensitivity to the compatibility factor. Further studies established that the presence of the compatibility factor confers the same race-specificity (for hml/hml corn) on the oat pathogen, *Cochliobolus victoriae*. The structure of this compatibility factor, HC-toxin, is known but the mode of action remains to be elucidated. Recently, an enzyme that inactivates HC-toxin has been identified in extracts from maize. The enzyme, HC-toxin reductase (HCTR), is detectable only in extracts from resistant (Hml) genotypes. This establishes HCTR activity as the biochemical phenotype of Hm1.

DISCLOSURE OF THE INVENTION

It has now been determined that the Hm1 gene can be used in conjunction with HC-toxin in a selectable marker system for use in maize transformation. When the cloned gene is linked to appropriate regulatory sequences for expression in plant cells and cotransformed into maize cells along with another quantitative or qualitative trait which is not selectable, it confers upon transformants a resistance to HC-toxin by virtue of the production of HCTR. The cells can continue to grow on medium containing the isolated HC-toxin. Nontransformed cells do not express the HCTR and are rapidly killed by the toxin the pathogen produces. The net effect is a tissue culture containing only transformed cells which can then be regenerated by known methods to form transformed shoots and even whole plants.

It has also been discovered that this gene can be inserted using conventional transformation methods into the genomes of maize varieties which lack the gene and are susceptible to disease caused by *C. carbonum*. Resulting transformants are resistant to the disease.

It has further been discovered that the HM1 resistance gene is one of a family of homologous disease resistance genes in maize and other crops. Accordingly, the present invention also encompasses methods for identification of homologous disease resistance genes by using this gene or a fragment thereof as a probe.

Materials and Methods

Genetic Materials and Propagation

Mutator stocks used in this work were obtained from Dr. D. Robertson, Iowa State University. Ac/Ds stocks used were obtained from D. I. Greenblatt, University of Connecticut. The methodology of HM1 mutant isolation was performed in the manner previously published by one of us [S. P. Briggs, Curr. Top. Plant Biochem. Physiol., 6:59 (1987)].

Inbred HM1 allele designations are: Pr, hm1-1; K61, hm1-2; P8, Hm1-A; Pr1, Hm1-Pr1; B79, Hm1-B79; 4Co63, Hm1-4C063; Pioneer PHV12, Hm1-PHV12.

Experimental Approach

Transposon-tagging is known to be a reliable tool for isolating genes from maize. The basic tenet of tranposon tagging is that DNA rearrangements (i.e., insertions or excisions) that are concomitant with genetic (phenotypic) changes define a causal relationship which identifies the rearranged DNA as the changed gene. Several independent events of this nature are accepted as proof of identity. As described herein, we have observed that 5 mutant alleles of HM1 are associated with insertions within a transcribed region (hm1-656::Mu1), hm1-1369::Mu3, Hm1-1062::dHbr, hm1-2355, hm1-1040::Spm), and 1 deletion allele Def(HM1)-1790 is associated with loss of the transcribed region. Finally, only the wild-type allele (Hm1-Pr1) produced a 1.3 kb mRNA.

The transposable element family Mutator is particularly effective for generating forward mutations. Germinal reversion of mutants back to wild-type is rare with Mutator-induced alleles. Somatic reversion has been observed, but the small somatic sectors typical of Mutator cannot be identified for traits that are not cell autonomous or are complex, such as disease lesion development. Therefore, to obtain multiple genetic events that were coincident with rearrangements of HM1, a strategy based upon independent forward mutations rather than reversions was used.

To identify co-segregation between HM1 and a restriction fragment, the segregating progeny were first classified by examining their DNA on Southern blots. The blots were hybridized with probes for RFLP loci that flank the locus; PIO200644 and PIO200044 (obtained from D. Grant, Pioneer Hi-Bred International, Inc.) map 5 cM proximal and distal to HM1, respectively (2; unpublished observations). Only progeny that inherited alleles at both loci from the same parent were used in the analysis. This approach permitted the identification of progeny which inherited the 10 cM block of chromosome 1 bounded by the RFLP loci. By grouping together progeny that inherited either the mutant allele, or the recessive tester allele with which the mutant allele was paired, and then comparing the two classes with each other, restriction fragments that were common to one progeny class and absent from the other were identified. This method established linkage between restriction fragments and the 10 cM block that contains HM1.

To directly determine the linkage between HM1 and a restriction fragment, linked fragments were cloned and used to prepare DNA hybridization probes. Probes were then hybridized to a Southern blot of DNA from 60 progeny of the backcross K61/Pr1 X K61. The backcross progeny were scored for inheritance of the HM1 alleles by inoculating them with conidia of the *C. carbonum* race 1 strain SB111, and for inheritance of the alternate alleles detected by the DNA probes. A comparison of the patterns of inheritance revealed the linkage relationships between the probes and HM1.

The RFLP loci described above, plus an RFLP locus that is detected by the probe NPI429, were used to identify the progenitor of the mutant alleles. We obtained NPI429 from T. Helentjaris, Native Plants, Inc.

Isolation of DNA and blot hybridization

Total DNA from the leaf tissue of maize, Sorghum (Pioneer inbred P285), and Coix (*Lachrymae jobi*) and seedling tissue of *Arabidopsis thaliana* L. (*Landsberg erecta*) was isolated by the urea extraction method as described in S. L. Dellaporta, J. Wood, J. B. Hicks, *Plant Mol Biol Rep,* 1, 18 (1983). Southern blots were prepared as described by Athma et al, *Genetics,* 128, 163 (1991). For RFLP analysis, DNA was transferred to nylon membranes (MSI from Fisher) and the hybridizations were performed as described above but without the addition of formamide. Probes were made from gel-purified DNA fragments and labeled by random priming (Amersham). The Mu1 specific probes was an internal 650 bp AvaI/BstEII fragment isolated from pA/B5; the plasmid was provided by L. Taylor, Stanford University. The Mu3 specific probe was the internal HindIII/XbaI fragment of a clone that was obtained from V. Chandler, University of Oregon. The Spm probes were pBx1 and pXS2.3 obtained from K. Cone, Brookhaven National Laboratory.

Isolation of RNA and Northern Blotting

Total RNA from 5 to 6 day-old etiolated seedlings was isolated by the guanidine thiocyanate method [P. Chomczynski and N. Sacchi, Anal Biochem 162, 156 (1987)]. Poly(A)+ RNA was enriched using the polyATtract mRNA isolation system of Promega. Samples (~15 ug) of poly(A)+ RNA were denatured using formaldehyde, fractionated in a 1.3% agarose gel, and blotted onto Hybond-N by standard techniques. DNA probes were radiolabeled by random priming and the blots were hybridized and washed as described.

Genomic Cloning

DNA isolated from homozygous mutant seedlings was digested with SstI or XhoI and the appropriate DNA fragments (as judged from the Southern blots) were purified by preparative gel electrophoresis and electroelution into dialysis tubing. This purified DNA was ligated to preannealed SstI or XhoI cut arms from the bacteriophage vector λsep6-lac5 obtained from R. Martienssen, Cold Spring Harbor Laboratory. Packaging into Gigapack Gold (Stratagene) and screening of the libraries were carried out according to the manufacturers instructions. All clones were subcloned into Bluescript SK+ (Stratagene) and maintained in the SURE strain (Stratagene) of *E. coli.*

PCR (Polymerase Chain Reaction) and Sequence Analysis

For analysis of DNA from the resistant progeny of the hm1-656::Mu1/hm1-1369::Mu3 heterozygote, primers homologous to sequences on each side of the insertion sites were used for PCR amplication. The primer sequences were: 5' CTG CTC ATG ACT CAT ATC AGG CGG TAG C 3' (SEQ ID NO. 3) AND 5' GAC CAG CCG ACG CAG CAG CCC CGC CTT C 3'(SEQ ID NO: 4). PCR conditions were as described by Perkin Elmer-Cetus, except that the reactions were performed in 20% glycerol. Reactions were heated to 94 C for 3 min, then cycled 40 times for 1 min at 94 C, 2 min at 65 C, and 2 min at 72 C; and finally extended for 15 min at 72C. The gel-purified PCR products were reamplified and directly sequenced using synthetic sequencing primers.

HM1 Mutants Derived from Mutator Stocks

Several mutant alleles of HM1 were recovered from Mutator element stocks, 4 of which were selected for further study. Criteria for selection included DNA hybridization data that ruled out pollen contamination as the source of the mutant alleles and a low frequency of susceptible progeny appearing within a family. RFLP loci were used to distinguish between the mutant alleles and the standard recessive alleles with which they had been paired. Segregating progeny were classified for inheritance of mutant alleles by use of the RFLP probes.

hm1-656::Mu1

Progeny produced by fertilizing plants of the genotype y wx gl1 Hm1-B79 Mutator (designated 81-82-9537 $Mu^2$ per se by D. Robertson) with pollen from the hybrid, K61/Pr, resulted in the recovery of 2 susceptible plants out of 253 progeny. Both susceptible plants were found to be carrying the mutant allele, hm1-656::Mu1, indicating that they arose as the result of a small somatic sector on the ear. Pollen from both plants was used to fertilize ears on the Pioneer inbred, PHV12.

When progeny from the cross hm1-656::Mu1/hm1-1 x Hm1-PHV12/Hm1-PHV12 were classified according to inheritance of the hm1-656::Mu1 allele (by using the RFLP loci), a pattern of hybridization with probe DNA from the Mu1 element was observed. A 3.2 kb SstI fragment co-segregated with the hm1-656::Mu1 allele. No exceptions to this were found in a sample of 92 progeny. The 3.2 kb fragment, which contained Mu1 plus some flanking DNA, was excised from a gel, cloned into the SstI site of λ sep6-lac5, subcloned into Bluescript SK+, restriction mapped, and used to prepare a probe from the DNA flanking the Mu1 insertion (designated *656).

The *656 probe was hybridized to a Southern blot of DNA from 4 different homozygous mutants. Classification using RFLP loci indicated that each of the mutant alleles was derived from the B79 inbred parent (Hm1-B79). The observation of polymorphisms showed that a DNA rearrangement took place in the cloned region concomitant with the generation of the mutations. With the enzyme used, hm1-1062::dHbr produces a fragment identical to B79. However, polymorphisms between hm1-1062::dHbr and B79 can be detected using other enzymes.

hm1-1369::Mu3

The hm1-1369::Mu3 allele was recovered as a single susceptible plant out of 230 progeny. The progeny were produced by pollinating plants of the genotype y wx gl1 Hm1-B79 Mutator (designated 81-82-9537 $Mu^2$ per se by Dr. Robertson) with the hybrid, K61/Pr (hm1-2/hm1-1).

The heterozygote, hm1-1369::Mu3/hm1-2, was self-pollinated and the progeny were classified using RFLP loci. Hybridization of a Mu3 probe revealed a co-segregating band. A 4.6 kb SstI fragment co-segregated with the hm1-1369::Mu3 allele. The signal intensity difference caused by 2 doses of the allele, when homozygous, permitted hm1-1369::Mu3 to be scored as a codominant marker, which increased the mapping resolution. No recombinants were observed in a sample of 60 progeny. The 4.6 kb fragment, which contained Mu3 plus flanking DNA, was excised from the gel and cloned into the SstI site of λ sep6-lac5 subcloned into Bluescript SK+, restriction mapped, and used to prepare a probe (designated *1369) from the DNA that flanked the Mu3 insertion.

The *1369 probe detected the same polymorphisms that had been revealed by the *656 probe, indicating that the Mu1 and Mu3 elements had inserted into the same restriction fragment. This conclusion was confirmed by comparison of the restriction maps of the 2 clones. An anomaly was revealed with SstI in which the hm1-656::Mu1 DNA gave a 3.2 kb fragment when hybridized with the *656 probe but a 1.0 kb fragment when the *1369 probe was used; other enzymes failed to detect this anomaly. DNA sequence analysis showed that the Mu1 element had created an SstI site upon insertion into HM1.

An effort was made to recover resistant progeny from the Mu alleles. The heterozygote, hm1-656::Mu1/hm1-1369::Mu3 was fertilized using pollen from the inbred Pr (hm1-1). From 500 progeny, 1 resistant plant was recovered. Examination of DNA from 10 susceptible siblings of the resistant plant confirmed that all three parental alleles were segregating as expected. Examination of DNA from the resistant plant revealed a progenitor-sized fragment from B79 (designated Hm1-B79R) plus the hm1-1 allele from Pt. This plant was self-pollinated. DNA from its progeny was examined using probes *1369, PIO200644, PIO200044, and NPI429. The same progeny were tested for susceptibility to infection by inoculating with SB111. The results confirmed that resistance was conferred by the Hm1-B79R allele. Homozygous Hm1-B79R progeny were identified. The site of insertion of Mu1/Mu3 was amplified by PCR and sequenced with no difference observed between the new allele and the B79 progenitor.

hm1-1062::dHbr

Progeny produced by pollinating the hybrid, K61/Pr (hm1-2/hm1-1), with plants of the genotype y wx g11 Hm1-B79 Mutator (designated 81-82-9539 $Mu^2$ per se by Dr. Robertson) resulted in the recovery of the hm1-1062::dHbr allele from 1 of 2 susceptible plants out of 483 progeny.

Hybridization with probes specific for Mu1, Mu3, Mu7, and Mu8 failed to identify a fragment that cosegregated with hm1-1062::dHbr. Hybridization with the *656 probe detected a polymorphism between hm1-1062::dHbr and the progenitor allele, Hm1-B79. We cloned a 3.1 kb XhoI fragment from the hm1-1062::dHbr mutant into λ sep6-lac5, using *656 as a probe. Restriction mapping confirmed the B79 structure with the exception of a small (approximately 400 bp) insertion into the SstI-XhoI fragment at the 3'-end of the clone. The identity of this insertion element has not been determined, but it lacks homology with Ac, Ds1, DS2, and Spm/En internal sequence probes and with the Mu terminal inverted repeat.

Def(HM1-1790)

Progeny produced by pollinating plants of the genotype y wx g11 Hm1-B79 Mutator (designated 81-82-9536 $Mu_2$ per se by D. Robertson) with the hybrid, K61/Pr (hm1-2/hm1-1), resulted in the recovery of the Def(HM1)-1790 allele from a single susceptible plant out of 345 progeny.

The Def(HM1)-1790 allele displays an aberrant transmission pattern. A Def(HM1)-1790/hm1-1 heterozygote was self-pollinated and the progeny were characterized using the flanking RFLP loci. Only 14 of 56 progeny were found to have inherited the Def(HM1)-1790 chromosome. When a heterozygote was fertilized using pollen from a wild-type stock (SB509), 8 of 25 progeny inherited the Def(HM1)-1790 chromosome. When the heterozygote was used as the pollen source to fertilize a wild-type inbred (W23), none of 32 progeny inherited the Def(HM1)-1790 chromosome. The results show that the Def(HM1)-1790 allele (or chromosome) was not transmitted through the pollen and was only poorly transmitted through the egg. Such a pattern of transmission is typical of a chromosomal deficiency. The *1369 probe did not hybridize with DNA from the Def(HM1)-1790 allele, confirming the presence of a deletion and showing that the cloned region lies within the deletion. Test crosses with br2, which maps within 0.1 cM of HM1, produced only wild-type progeny. Likewise, both PIO200644 and PIO200044 detected 2 alleles in progeny that inherited Def(HM1)-1790. Therefore, the deletion cannot encompass more than 5 cM of the chromosome, being bounded by br2 and one of the RFLP loci.

An HM1 mutant derived from an Ac/Ds stock

An allele, Hm1-1040::Spm, was recovered from the inbred 4Co63; the P-VV allele (Ac inserted into the P1 gene) had been backcrossed into this version of 4Co63. This allele was selected for study because it appeared to arise as a large tassel sector. The hybrid K61/Pr (hm1-2/hm1-1) was fertilized using pollen from the P-VV/P-WW) inbred 4Co63 (Hm1-4Co63/Hm1-4Co63), designated 610417(X) by I. Greenblatt (personal communication). Seventeen males were used to produce 32 ears. Only 2 ears bore susceptible progeny and both were derived from male plant number 16. The cross 741-11 x 741-9 plant 16 yielded 47 susceptible progeny out of 323. The cross 741-13 X 741-9 plant 16 yielded 16 susceptible progeny out of 323. The results are best explained by a single mutagenic event that occurred during tassel development, giving rise to many gametes bearing the same mutation.

Genetic tests showed that Ac had not transposed in the hm1-1040::dSpm mutant; Ac, Ds1, and Ds2 probes failed to identify a restriction fragment that cosegregated with hm1-1040::dSpm. Examination of DNA from the hm1-1040::dSpm mutant by hybridization with the *1369 probe revealed an 11.0 kb SstI restriction fragment that was 6 kb larger than the Hm1-4Co63 progenitor allele. This fragment was cloned into λ sep6-lac5. Hybridization of various probes to DNA from the clone identified the insertion as an Spm/En homologous element.

Natural Variation

The Hm1 parental alleles from which the mutants described in this report were derived provide complete resistance to *C. carbonum* race 1 throughout the development of the plant. In contrast, the Hm1-A allele, found in the inbred P8, provides partial resistance that increases as the plant develops. Examination of DNA from P8 by hybridization with the *1369 probe showed that the cloned region is duplicated. The duplicate locus segregates independently of HM1. The relationship between the pattern of expression and the duplication has not been established. The *1369 probe hybridized well with DNA from the grasses Sorghum and Coix but poorly with DNA from Arabidopsis. Poly(A)+ RNA from our mutants and from the inbreds K61 (hm1-2) and Pr1 (Hm1-Pr1) was blotted and hybridized with the *1062 probe. A 1.3 kb mRNA band was present only in the Pr1 lanes. The susceptible genotypes either had no detectable hybridizing mRNA or the size was aberrant. In all cases, the signal was extremely weak.

These results establish that all or a sufficient part of the HM1 gene has been cloned and sequenced, with genomic and cDNA sequences as shown in SEQUENCE I.D. No. 1 and SEQUENCE I.D. No. 2, respectively. Recessive alleles of the gene clearly contain homologous DNA (e.g., hm1-1 and hm1-2). This stands in contrast to the 2 fungal plant pathogen genes that have been cloned which control race specificity:: TOX2 confers race 1 type pathogenicity upon *C. carbonum* (Walton, personal communication) and avr9 confers race specific avirulence upon *Cladosporium fulvum*; both genes are missing in strains that lack their corresponding functions.

Resistance appears to differ from susceptible at the transcriptional level, at least among the small samples of alleles that were examined. This indicates that susceptible genotypes do not possess an alternative form of HM1 with specificity for a substrate other than HC-toxin. This result also suggests that the only function of HM1 in young leaf tissue is to provide resistance, since the HM1 mutations are not pleiotropic.

Use in Disease Resistance

Plants

The preferred embodiment of this method involves inserting the HM1 gene into the genome of the plant in proper reading frame, together with transcription initiator and promoter sequences active in the plant. Transcription and translation of the gene under control of the regulatory sequences causes resistance to the disease caused by *C. carbonum*.

The plant must be a plant susceptible to infection and damage by *C. carbonum*. These include corn (*Zea mays*). However, this is not to be construed as limiting, inasmuch as this species is among the most difficult commercial crops to reliably transform and regenerate, and this pathogen can also infect certain other crops. Thus the methods of this invention are readily applicable via conventional techniques to other plant species, if they are found to be susceptible to *C. carbonum*, including, without limitation, species from the genera Allium, Antirrhinum, Arabidopsis, Arachis, Asparagus, Atropa, Avena, Beta, Brassica, Browallia, Capsicum, Cicer, Cicla, Citrullus, Citrus, Cucumis, Cucurbita, Datura Daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Manihot, Medicago, Nasturtium, Nicotiana, Oryza, Pelargonium, Persea, Petunia, Phaseolus, Pisum, Ranunculus, Raphanus, Ricinus, Saccharum, Secale, Senecio, Setaria, Solanum, Spinacia, Trifolium, Triticum, Bromus, Cichorium, Hyoscyamus, Linum, Nemesia, Panicum, Onobrychis, Pennisetum, Salpiglossis, Sinapis, Trigonella, and Vigna.

Preferred plants that can be transformed according to the methods of this invention are cereal crops, including maize, rye, barley, wheat, sorghum, oats, millet, rice, triticale, sunflower, alfalfa, rapeseed and soybean.

Numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gens. In addition, the plant expression cassette preferably includes a strong constitutive promoter sequence at one end to cause the gens to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, Iowa, as disclosed in U.S. patent application Ser. No. 07/785,648, filed Oct. 31, 1991, now abandoned, the disclosures of which are hereby incorporated herein by reference. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, genomic, cDNA or synthetic DNA encoding the HM1 gene may be used in this invention. The vector of interest may also be constructed partially from a cDNA clone and partially from a genomic clone, etc. Genetic constructs are made which contain the necessary regulatory sequences to provide for efficient expression of the gene in the host cell. According to this invention, the genetic construct will contain (a) a first genetic sequence consisting of the HM1 gene, and (b) one or more regulatory sequences operably linked on either side of the structural gene of interest. Typically, the regulatory sequences will be selected from the group comprising of promoters and terminators. The regulatory sequences may be from autologous or heterologous sources.

Promoters that may be used in the genetic sequence include nos, ocs, FMV and CaMV promoters.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al., *J. Molecular and App. Gen.*, 1:483–498 (1982)), and the promoter of the cholorophyll a-b binding protein. These two promoters are known to be light-induced, in eukaryotic plant cells (see, for example, Genetic Engineering of Plants, An Agricultural Perspective, A. Cashmore, Pelham, New York, 1983, pp. 29–38, G. Coruzzi et al., *J. Biol. Chem.*, 258:1399 (1983), and P. Dunsmuir, et al., *J. Molecular and App. Gen.*, 2:285 (1983)).

The expression cassette comprising the HM1 gene operably linked to the desired control sequences can be ligated into a suitable cloning vector. In general, plasmid or vital (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. However, in the context of this invention, the HM1 gene can also serve as the selectable marker in the transformation process. After the genetic material is introduced into the target cells, successfully transformed cells and/or colonies of cells can be isolated by selection on the basis of survival in the presence of HC-toxin.

Typically, an intermediate host cell will be used in the practice of this invention to increase the copy number of the cloning vector. With an increased copy number, the vector containing the HM1 gene can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention.

The isolated cloning vector will then be introduced into the plant cell using any convenient technique, including electropotation (in protoplasts), retroviruses, microparticle bombardment, and microinjection into cells from monocotyledonous or dicotyledonous plants in cell or tissue culture to provide transformed plant cells containing as foreign DNA at least one copy of the plant expression cassette containing the HM1 gene. Using known techniques, protoplasts can be regenerated and cell or tissue culture can be regenerated to form whole fertile plants which carry and express the HM1 gene according to this invention. Accordingly, a highly preferred embodiment of the present invention is a transformed maize plant, the cells of which contain as foreign DNA at least one copy of an expression cassette of this invention containing the HM1 gene.

Finally, this invention provides methods of imparting resistance to diseases caused by *C. carbonum* to plants of a susceptible taxon, comprising the steps of:

a) culturing cells or tissues from at least one plant from the taxon, b) introducing into the cells or tissue culture at least one copy of an expression cassette comprising the HM1 gene operably linked to plant regulatory sequences which cause the expression of the gene in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens,* which can then be used to transfer the vector into susceptible plant cells, primarily from dicotyledonous species. Thus, this invention provides a method for imparting antimicrobial activity and disease resistance in *Agrobacterium tumefaciens*-susceptible dicotyledonous plants in which the expression cassette is introduced into the cells by infecting the cells with *Agrobacterium tumefaciens,* a plasmid of which has been modified to include a plant expression cassette of this invention.

Use as a Probe

This invention also provides methods of isolating disease resistance genes from maize and other species, by using the HM1 gene as a probe. It has been determined that HM1 is homologous to a family of disease resistance genes in maize and other species such as Arabidopsis, and this gene provides a probe which can be used, by hybridizing the gene with restriction digests of "target" genomic DNA, to count the disease resistance genes therein. It can also be used, by hybridization against a genomic library from the subject organism, to identify positive colonies which can then be cloned and sequenced. These techniques are well known and widely published, as seen by the published series Current Protocols in Molecular Biology, F. M Ausubel, ed., (Wylie 1987-89), which have disclosed such methods for the last eight years, and the disclosures of which are hereby incorporated herein by reference. The novel aspect claimed herein is the use of the HM1 gene or a fragment thereof in those methods as a highly selective probe for specific identification of disease resistance genes.

---

What is claimed is:

1. A purified DNA sequence comprising the Hm1 gene of maize.

2. A DNA sequence having at least 90% sequence identity to the sequence of SEQUENCE I.D. NO. 1 or SEQUENCE I.D. NO. 2.

3. An expression cassette containing the DNA sequence of claim 1 or 2 operably linked to plant regulatory sequences which cause the expression of the DNA sequence in plant cells.

4. A bacterial transformation vector comprising an expression cassette according to claim 3, operably linked to bacterial regulatory sequences which cause replication of the expression cassette in bacterial cells.

5. Bacterial cells containing as a foreign plasmid at least one copy of a bacterial transformation vector according to claim 4.

6. Transformed plant cells containing at least one copy of the expression cassette of claim 3.

7. A transformed plant comprising transformed cells according to claim 6.

8. A method of identifying plant transformation using *C. carbonum* or the toxin produced by *C. Carbonum* as a phytotoxic marker, comprising the steps of:

a) culturing cells or tissues from a selected target plant, b) introducing into the cell or tissue culture at least one copy of an expression cassette according to claim 3, c) introducing *C. carbonum* or the toxin it produces into the cell or tissue culture and d) identifying transformed cells as the surviving cells in the cell or tissue culture.

9. A method of imparting resistance to diseases caused by *C. carbonum* to plants of a susceptible taxon, comprising the steps of:

a) culturing cells or tissues from at least one plant from the taxon, b) introducing into the cells or tissue culture at least one copy of an expression cassette comprising the Hm1 gene operably linked to plant regulatory sequences which cause the expression of the gene in the cells, and c) regenerating disease-resistant whole plants from the cell or tissue culture.

10. A method of identifying disease resistance genes which are homologous to the maize Hm1 gene in the genome of a plant, comprising identifying sequences which hybridize with the Hm1 gene or a fragment thereof, generating transgenic plants containing and expressing the homologous genes, and screening said plants for disease resistance.

11. A method according to claim 10 wherein the sequences are identified by hybridizing a cDNA library or a restriction digest of genomic DNA from the plant with the HM1 gene or a fragment thereof.

* * * * *